(12) United States Patent
Cane' et al.

(10) Patent No.: US 11,273,253 B2
(45) Date of Patent: Mar. 15, 2022

(54) SYRINGE ACTUATING DEVICE

(71) Applicant: CANE' S.P.A., Rivoli (IT)

(72) Inventors: Claudio Cane', Rivoli (IT); Mario Cane', Rivoli (IT); Paolo Cane', Rivoli (IT)

(73) Assignee: CANE' S.P.A., Rivoli (IT)

(*) Notice: Subject to any disclaimer, the term of this patent is extended or adjusted under 35 U.S.C. 154(b) by 108 days.

(21) Appl. No.: 16/334,259

(22) PCT Filed: Sep. 15, 2017

(86) PCT No.: PCT/IB2017/055595
§ 371 (c)(1),
(2) Date: Mar. 18, 2019

(87) PCT Pub. No.: WO2018/051281
PCT Pub. Date: Mar. 22, 2018

(65) Prior Publication Data
US 2019/0209772 A1    Jul. 11, 2019

(30) Foreign Application Priority Data

Sep. 19, 2016    (IT) .................. 102016000093803

(51) Int. Cl.
*A61M 5/142*    (2006.01)
*A61M 5/145*    (2006.01)
*A61M 5/168*    (2006.01)

(52) U.S. Cl.
CPC .......... *A61M 5/1422* (2013.01); *A61M 5/142* (2013.01); *A61M 5/14244* (2013.01);
(Continued)

(58) Field of Classification Search
CPC ............ A61M 5/1422; A61M 5/14546; A61M 5/14566; A61M 5/16827;
(Continued)

(56) References Cited

U.S. PATENT DOCUMENTS 6,447,487 B1    9/2002 Cane'
D659,234 S    5/2012 Cane'
(Continued)

FOREIGN PATENT DOCUMENTS

WO    2011/154928 A1    12/2011

*Primary Examiner* — Amber R Stiles
*Assistant Examiner* — Avery Smale
(74) *Attorney, Agent, or Firm* — Howson & Howson LLP

(57) ABSTRACT

A syringe actuating device has a first supporting plate in which an axial guide for a primary rod is defined and a second supporting plate defining at least two engagement seats for bases of corresponding syringes having a barrel and a sliding plunger. A guide for axial sliding of a corresponding secondary rod with a head is associated with each of the engagement seats. The device also includes an electric motor having a driving shaft, an assembly for converting rotary motion of the shaft into translational motion of the primary rod and a pair of connecting arms adapted to transmit sliding motion of the primary rod to a corresponding one of the secondary rods. Rotary movement of the driving shaft causes sliding of the secondary rods and, consequently, sliding of the plungers when the syringes are engaged in corresponding engagement seats and the plungers are in abutment against the heads.

9 Claims, 3 Drawing Sheets

(52) U.S. Cl.
CPC .... *A61M 5/14546* (2013.01); *A61M 5/14566* (2013.01); *A61M 5/16827* (2013.01); *A61M 2005/14573* (2013.01)

(58) Field of Classification Search
CPC .... A61M 2005/14573; A61M 5/14244; A61M 5/142; A61M 5/1407; A61M 5/1408
See application file for complete search history.

(56) References Cited

U.S. PATENT DOCUMENTS

| | | |
|---|---|---|
| 9,220,835 B2 | 12/2015 | Cane' |
| 9,289,549 B2 | 3/2016 | Cane' |
| 9,463,271 B2 | 10/2016 | Cane' |
| 2006/0184124 A1 | 8/2006 | Cowan et al. |
| 2008/0045925 A1 | 2/2008 | Stepovich et al. |
| 2010/0030153 A1* | 2/2010 | Neer ................ A61M 5/14546 604/154 |
| 2010/0143864 A1 | 6/2010 | An |
| 2012/0143133 A1* | 6/2012 | Congnome Cane' ........................ A61M 5/1422 604/131 |
| 2012/0245560 A1* | 9/2012 | Hochman ........... A61M 5/1452 604/518 |
| 2015/0038906 A1* | 2/2015 | Cane' ............... A61M 5/14566 604/152 |
| 2017/0340810 A1 | 11/2017 | Cane' et al. |

\* cited by examiner

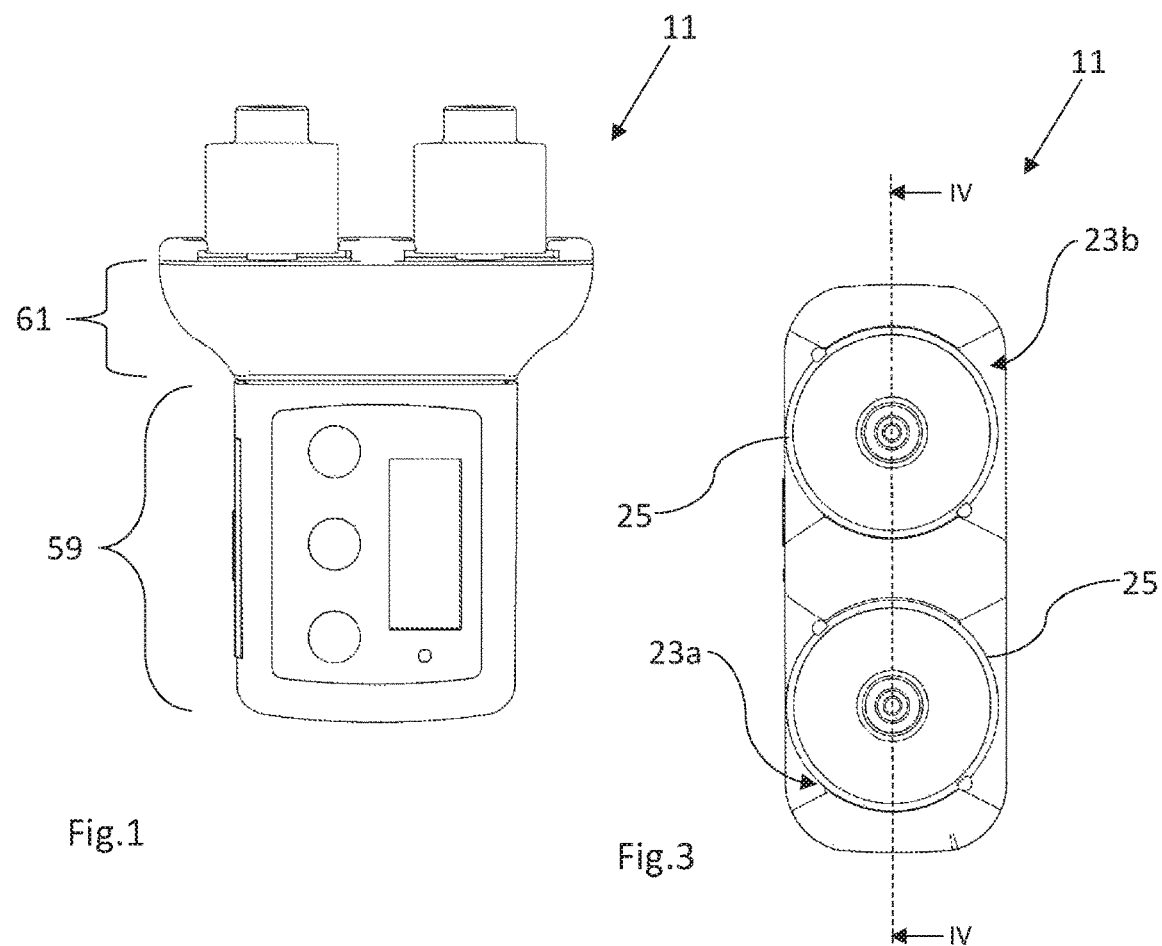
Fig.1
Fig.3
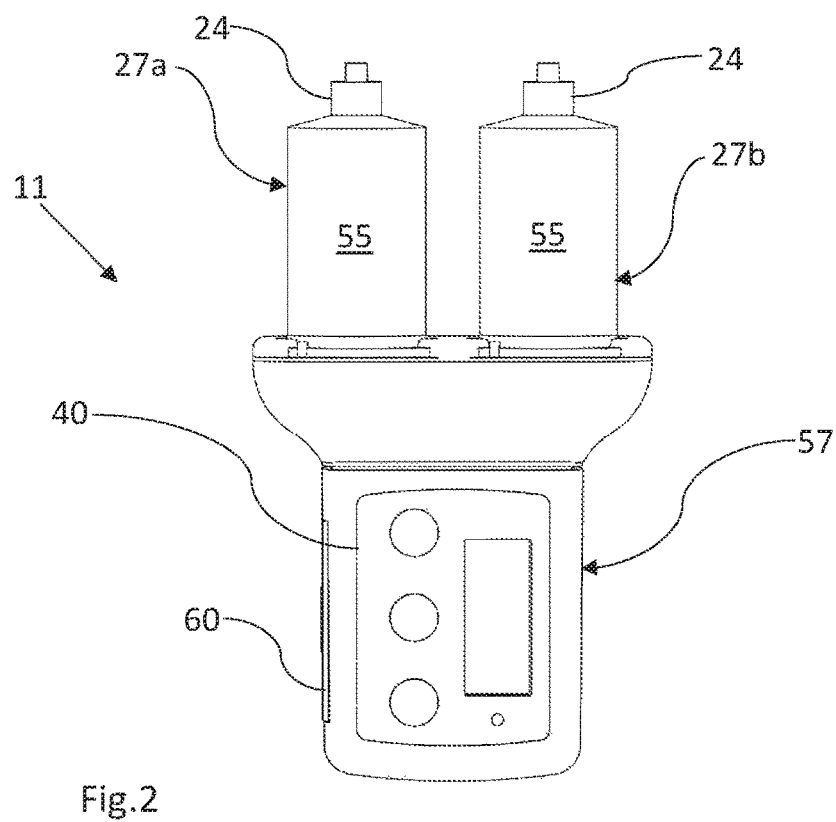
Fig.2

SYRINGE ACTUATING DEVICE

TECHNICAL FIELD

The invention concerns a syringe actuating device. More particularly, but not exclusively, the invention concerns an electromechanical syringe actuating device, adapted to be used for the programmed infusion of substances, especially drugs, into the body of a living being.

PRIOR ART

There are known syringes for drug infusion into the body of a living being and programmable electromechanical actuating devices for controlling drug infusion in automatic manner, based on a specific medical prescription.

The prior art devices are generally intended to control a single syringe at a time. When the substance to be infused has run out, the syringe associated with the device is replaced, if necessary, with a new syringe filled with drug. EP 2832389 (A1) discloses an example of portable infusion device of the above kind. In the past, also syringe actuating devices capable of controlling infusion through two or more syringes simultaneously have been developed. EP 2460547 (A1) discloses a device of this kind.

The need to control infusion through two or more syringes associated with a single device can be determined by several factors. For instance, such a need may arise because the therapy requires infusion of high drug amounts per time unit, or because more kinds of drugs are to be simultaneously infused at different sites of the body, or because it is desired to infuse a same drug at more sites simultaneously, in order to increase the effectiveness of the same drug without encountering the risk of excessive infusion at a single site (what could occur in case of use of "Y"-shaped connectors connected to a single syringe, if one branch becomes obstructed), or yet because a high drug supply has to be available since the therapy is particularly long and cannot be frequently interrupted for substituting the exhausted syringe.

In all the above circumstances, and in other ones, the need is felt for a syringe actuating device which is compact and portable, lightweight, simple to be used and reliable. The prior art devices capable of simultaneously actuating more syringes are actually complex to be manufactured and consequently expensive.

Therefore, it is a first object of the invention to overcome the drawbacks of the prior art, by providing a syringe actuating device meeting the above requirements.

It is another object of the invention to provide a syringe actuating device which is applicable in the medical field for treatments and therapies of various kinds, both for human beings and for animals.

It is a further, but not the last object of the invention to provide a device capable of actuating a plurality of syringes, more particularly at least two syringes, which is simple to be used and which therefore can be controlled autonomously, that is without the help of supporting persons, also by patients with movement difficulties.

The above and other objects are achieved by means of the syringe actuating device as claimed in the appended claims.

DESCRIPTION OF THE INVENTION

The syringe actuating device made in accordance with a preferred embodiment of the invention mainly includes a first supporting plate in which an axial guide for a primary rod is defined. In an embodiment, said axial guide may consist of a hole passing through the supporting plate. In other embodiments, the guide may consist of a sleeve or a ferrule joined to the plate or made integrally therewith and defining a passageway for the primary rod passing through the supporting plate. The device further includes a second supporting plate defining at least two engagement seats for the bases of corresponding syringes. "Base of the syringe" denotes the open end portion located on the opposite side of the syringe barrel relative to the tapered opening, generally provided with a Luer-Lock connection, for drug delivery during infusion. In accordance with a preferred embodiment of the invention, the engagement seats are made so that they can receive the base of a conventional disposable syringe provided with radially projecting wings. Consequently, the engagement seat is substantially circular and is surrounded by a pair of diametrically opposite, interrupted annular grooves, defining the female part of a bayonet coupling for the syringe. A guide for the axial sliding of a corresponding secondary rod is associated with each of the engagement seats for the syringes. In an embodiment of the invention, the guides for the axial sliding of the secondary rods are defined by corresponding holes passing through the secondary plate. In other embodiments, said guides are defined by ferrules or sleeves joined to the secondary plate or made integrally therewith. The ferrules or sleeves define corresponding passageways through the plate for corresponding secondary rods. The secondary rod is adapted to cause the sliding of the syringe plunger within the syringe barrel, thereby causing the outflow of the substance, e.g. a drug, contained in the syringe barrel. Drug outflow takes place through the front opening, from where the drug arrives, generally though a flexible duct, into the body of the living being.

Preferably, the guides for the axial sliding of the primary rod and the secondary rods have an internal sliding surface made of a material with a low frictional coefficient or having undergone a treatment for lowering the frictional coefficient. Advantageously, jamming of the rod while the latter is sliding in the guide perpendicularly to the plate is thus prevented.

The device according to the invention further includes an electric motor having a rotatable driving shaft. Preferably, the electric motor is controlled by a programmable electronic control unit and is supplied by a battery embodied in the device.

Preferably, an assembly for converting the rotary motion of the driving shaft of the electric motor into a translational motion of the primary rod is provided between the driving shaft of the motor and the primary rod. Preferably, according to the invention, the motion converting assembly includes a pinion associated with the driving shaft of the electric motor and a gear ring of which the teeth are engaged in the pinion. The gear ring surrounds an internally threaded screw nut cooperating with the outer thread of the primary rod. The rotation of the screw nut caused by the rotation of the gear ring induced by the rotation of the pinion and of the driving shaft of the electric motor causes the axial sliding of the primary rod through the first supporting plate. The screw nut is rotatably supported by a third supporting plate of the device.

Advantageously, according to the invention, the device is equipped with at least one pair of connecting arms adapted to transmit the axial sliding motion of the primary rod to a corresponding one of said secondary rods. The arms may be separate and radially fastened to the primary rod and a corresponding secondary rod. Therefore, according to the invention, the rotary motion of the driving shaft of the electric motor causes sliding of the heads of the secondary rods and, consequently, the sliding of the plungers of the syringes, when the latter are engaged in the corresponding engagement seats of the first plate.

The three plates of the device and the other electromechanical members are housed within a casing. In a preferred embodiment of the invention, the casing comprises a main portion and an interface portion. Preferably, the motor and the motion converting assembly are housed in the main portion. Preferably, moreover, the main portion has a constant cross-section along an axis parallel to the primary rod: The interface portion preferably has on the contrary a bell-shaped cross-section that widens in a direction away from the main portion and parallel to the axis of the primary rod. The interface portion internally defines a chamber for the sliding of the connecting arms, and externally carries, at the end opposite to the main portion, the second plate on which the engagement seats for the syringes are defined. The bell shape widening outwards further allows receiving a second plate equipped with two or more engagement seats for corresponding syringes, by keeping the size of the casing of the device in the whole compact.

The plates of the device and the casing may be made of various materials, e.g. plastics or metal, preferably aluminium. Moreover, the plates are parallel to each other and, moreover, the second plate preferably has no openings, apart from the opening for the passage of the corresponding sliding secondary rods.

In a preferred embodiment of the invention, the guides for the secondary rods are so constructed as to substantially prevent inlet of liquid from the outside, at least under the normal conditions of use of the device, for instance when it is worn under a shower or in the normal activities for the care of the personal hygiene. Moreover, a ring-shaped sealing gasket preventing the inlet of liquid into the casing under the aforesaid normal conditions of use is preferably provided between the interface portion and the first plate and between the second plate and the interface portion.

Advantageously, in accordance with a preferred embodiment of the invention, the guides for the secondary rods include sealing rings, e.g. consisting of O-rings, in order to improve the tight sealing of the device against the inlet of liquids and humidity from the outside.

In this manner, advantageously, it is possible to build a substantially tightly-sealed actuating device, which therefore can be worn even under high humidity conditions or in the presence of liquids, for instance during the activities for the care of the personal hygiene.

In the alternative, it is also possible to build the first and/or the second supporting plate open, e.g. bored in order to reduce their weight, or as a supporting frame fastened to the walls of the casing of the device.

Advantageously, the device according to the invention allows actuating at least two syringes at the same time by means of a single electric motor and therefore it is compact and cheap. Advantageously, moreover, the device can be made also with more than two connecting arms and as many syringe engagement seats, in a cross-like or star-like arrangement, in order to actuate four or more syringes.

BRIEF DESCRIPTION OF THE FIGURES

Some preferred embodiments of the invention will be provided by way of non-limiting example with reference to the accompanying Figures, in which:

FIG. 1 is a front view of the device according to the invention, without syringes;

FIG. 2 is a front view of the device shown in FIG. 1, when equipped with a pair of syringes;

FIG. 3 is a top view of the device shown in FIG. 1, when equipped with a pair of syringes;

DESCRIPTION OF SOME PREFERRED EMBODIMENTS OF THE INVENTION

Figure 4A:
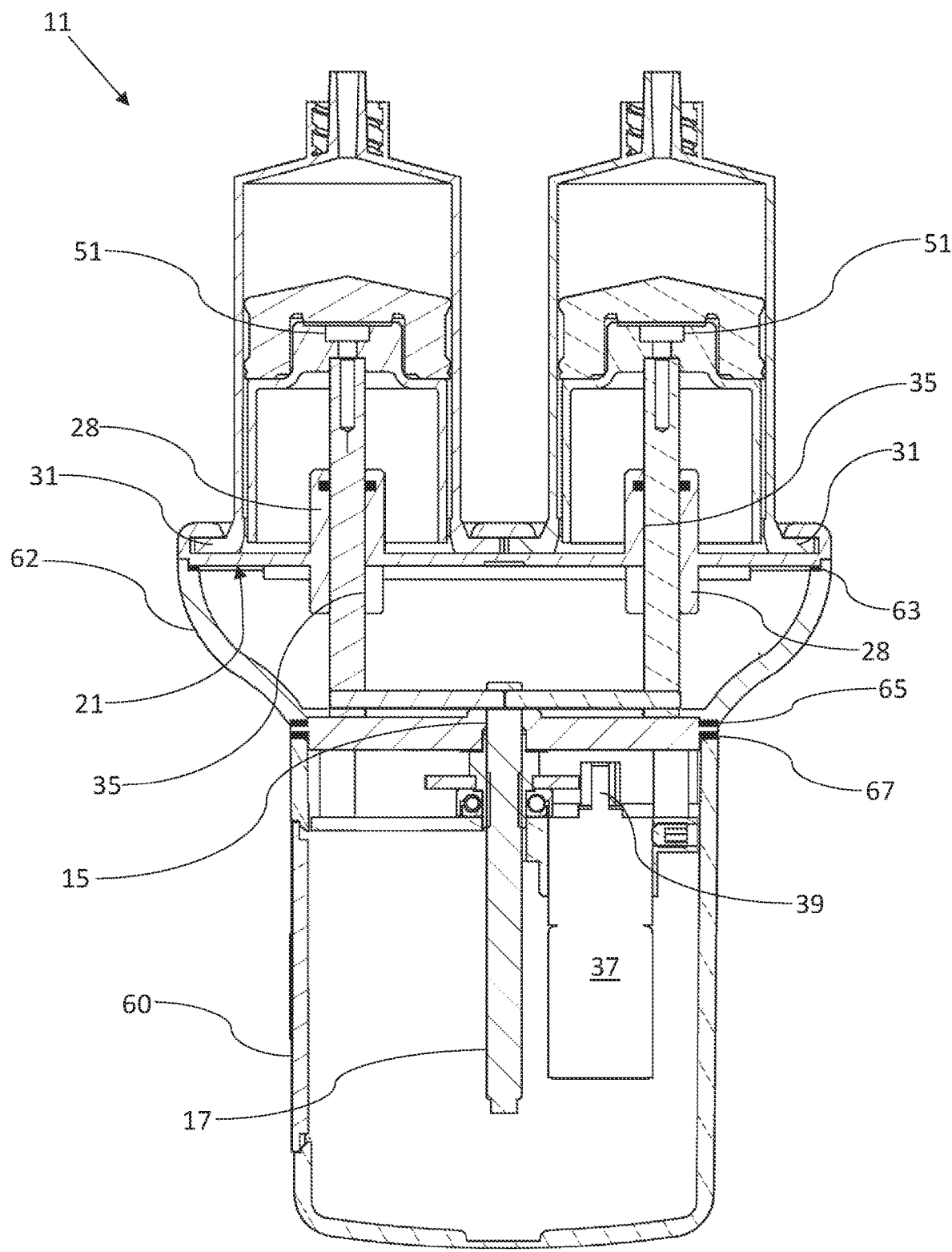
FIG. 4A is a sectional view, taken along a plane IV-IV, of the device shown in FIG. 1, when equipped with a pair of syringes, at the start of the infusion.

Referring to the accompanying Figures, device 11 made in accordance with a preferred embodiment of the invention includes a first supporting plate or frame 13. An axial guide 15 for a threaded primary rod 17 is defined in plate 13. According to the invention, plate 13 is made of plastics or more preferably of metal, e.g. aluminium. Primary rod 13 passes through said first plate 13 within axial guide 15. In the illustrated embodiment, axial guide 15 consists of a corresponding hole passing through plate 13. In the illustrated embodiment, axial guide 15 is defined substantially centrally of plate 13, which has, in plan view, an approximatively rectangular shape with rounded corners. Always referring to the illustrated embodiment, plate 13 has no further opening besides the hole defining axial guide 15. Device 11 further includes a second supporting plate or frame 21. Two engagement seats 23a, 23b for the open rear base or end 25 of a corresponding syringe 27a, 27b are defined in plate 21. Said base 25 is defined in syringe barrel 55 on the side opposite opening 24 provided with a Luer-Lock connection and serving for drug delivery during infusion. Syringes 27a, 27b may be conventional disposable syringes made of plastic material and provided with radially projecting wings 31 at base 25. A guide 26 for the axial sliding of a corresponding secondary rod 29a, 29b is associated with each engagement seat 23a, 23b. Guides 26 are located substantially centrally of engagement seats 23a, 23b. Secondary rods 29a, 29b pass through the second plate 21 within corresponding guides 26.

In the illustrated example, seats 23a, 23b are made so that they can house base 25 of a disposable syringe 27a, 27b provided with radially projecting wings 31. Consequently, each seat 23a, 23b is substantially circular and is surrounded by a pair of diametrically opposite and interrupted annular grooves 33 defining the female part of a bayonet-like coupling for the corresponding syringe 27a, 27b.

In the illustrated example, guides 26 are made as ferrules 28 integrally made with supporting plate 21, which will be preferably made of aluminium. Moreover, ferrules 28 have an internal surface with low frictional coefficient, made for instance of anodised aluminium, in order to make sliding of secondary rods 29a, 29b in the corresponding ferrule 28 easier. Advantageously, in accordance with this embodiment of the invention, the second plate 21 has no further opening besides holes 35 provided in ferrules 28 for the passage of secondary rods 29a, 29b. As it will become more apparent from the following description, the second plate 21 separates the environment outside device 11, which is faced by syringe engagement seats 23a, 23b, from the environment inside device 11. Preferably, ferrule 28 further defines a substantially tight seal with respect to the corresponding secondary rod 29 a, 29b, thereby making device 11 substantially tightly sealed. A sealing gasket 19, made in the illustrated embodiment as an O-ring of rubber or other suitable material, is optionally provided between ferrules 28 and secondary rods 29a, 29b. Gasket 19 determines a more effective tight seal between a ferrule 28 and the corresponding secondary rod 29a, 29b and prevents humidity and liquids from passing through ferrules 28.

Device 11 according to the invention further includes an electric motor 37 having a rotatable driving shaft 39. Preferably, electric motor 37 is controlled by a programmable electronic control unit associated with a control panel 40 accessible from the outside of device 11 and is supplied by a battery. Preferably, both the control unit and the battery will be housed within device 11.

An assembly for converting the rotary motion of driving shaft 39 of electric motor 37 into a translational motion of primary rod 17 is provided between driving shaft 39 of motor 37 and primary rod 17. Preferably, according to the invention, the motion converting assembly includes a pinion 41 associated with driving shaft 39 of electric motor 37 and a gear ring 43 engaged in pinion 41. Gear ring 43 surrounds an internally threaded screw nut 45 cooperating with the external thread of primary rod 17. The rotation of screw nut 45, caused by the rotation of gear ring 43 induced by the rotation of pinion 41 and driving shaft 39 of electric motor 37, causes the axial sliding of externally threaded primary rod 17 through the first supporting plate 13 within axial guide 15. Screw nut 45 is rotatably supported by a third supporting plate or frame 47 of device 11, to which motor 37 is fastened. Moreover, a thrust ball bearing 48 is preferably provided between plate 47 and screw nut 45.

Advantageously, according to the invention, device 11 is equipped with at least one pair of connecting arms 49a, 49b adapted to transmit the axial sliding motion of primary rod 17 to a corresponding one of said secondary rods 29a, 29b. In the illustrated embodiment, arms 49a, 49b are separate and are firmly fastened to primary rod 17 and secondary rods 29a, 29b, which will be provided with corresponding radial holes for receiving the ends of connecting arms 49a, 49b. In other embodiments, connecting arms 49a, 49b could be made as a single piece, and in yet other embodiments primary rod 17, connecting arms 49a, 49b and secondary rods 29a, 29b could be made as a single piece, thereby forming a single component. Connecting arms 49a, 49b are arranged substantially perpendicularly to primary rod 17 and secondary rods 29a, 29b. The assembly consisting of primary rod 17, connecting arms 49a, 49b and secondary rods 29a, 29b defines a substantially fork-like configuration. Therefore, according to the invention, the rotary movement of driving shaft 39 of electric motor 37 causes the axial sliding of heads 51 of secondary rods 29a, 29b and, consequently, the sliding of plungers 53 in barrels 55 of syringes 27a, 27b, when said syringes are engaged in the corresponding engagement seats 23a, 23b.

Referring in particular to FIG. 4A, device 11 is shown in the infusion start configuration, i.e. when syringes 27a, 27b inserted into engagement seats 23a, 23b are filled with liquid and the corresponding plungers 53 are wholly withdrawn. In such a configuration, connecting arms 49a, 49b are in a wholly withdrawn position, close to the first plate 13. Primary rod 17 and secondary rods 29a, 29b also are wholly withdrawn.

Figure 4B:
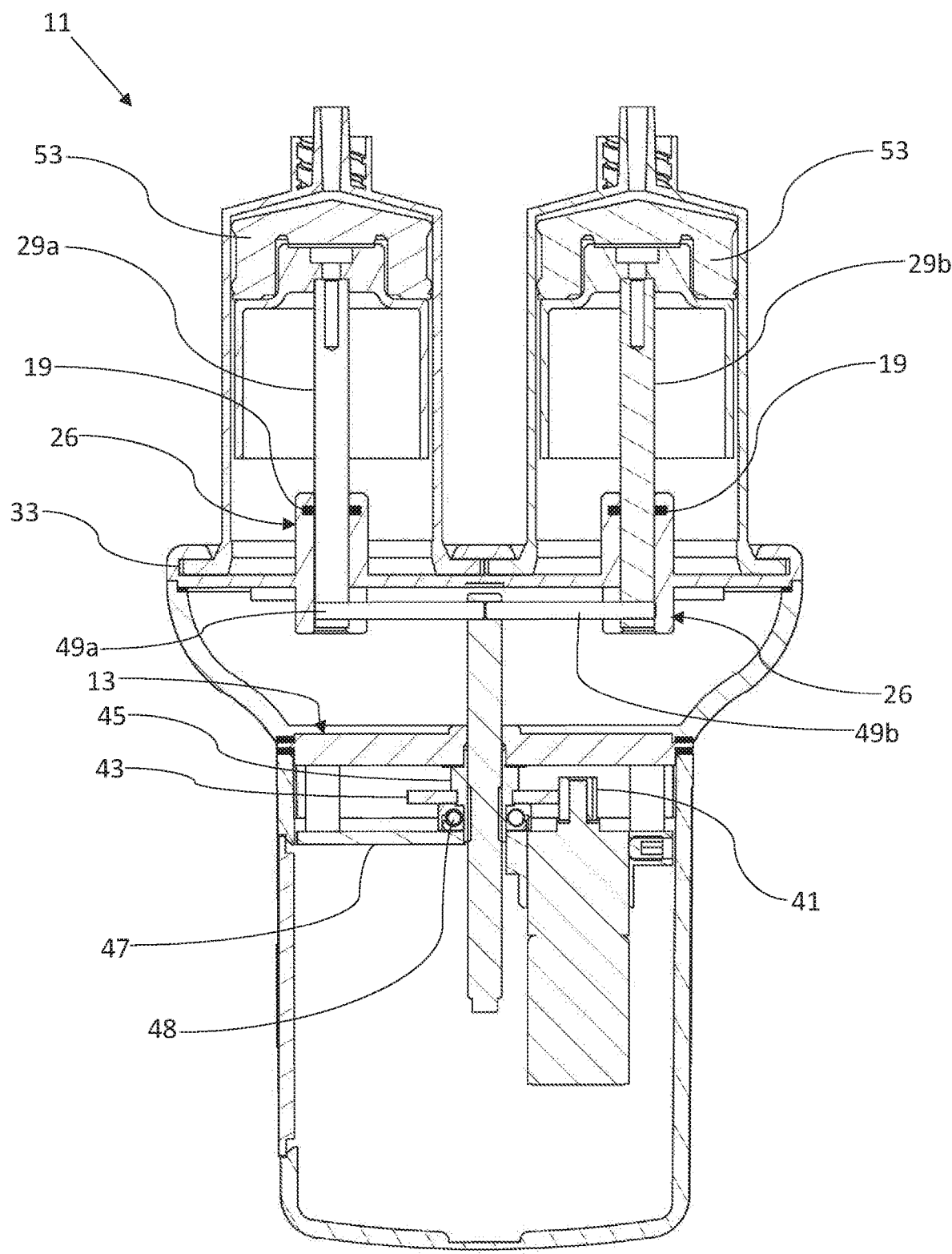
FIG. 4B is a sectional view, taken along a plane IV-IV, of the device shown in FIG. 1, when equipped with a pair of syringes, at the end of the infusion.

Referring now to FIG. 4B, device 11 is shown in the infusion end configuration, i.e. when syringes 27a, 27b inserted into engagement seats 23a, 23b no longer contain liquid and the corresponding plungers 53 are wholly advanced towards opening 24 of the front end of the syringe. In such a configuration, connecting arms 49a, 49b are in a wholly advanced position close to the second plate 21. Primary rod 17 and secondary rods 29a, 29b also are wholly advanced.

In the illustrated embodiment, the first supporting plate 13 and the second supporting plate 21 are parallel to each other and are firmly associated along their corresponding perimeters inside a casing 57 of device 11, also housing motor 37 and the motion converting assembly.

In the illustrated embodiment of the invention, casing 57 includes a main portion 59 and an interface portion 61, mutually connected. Motor 37 and the motion converting assembly are housed in the main portion. Moreover, the battery supplying the device with power and the electronic control unit of the device are housed in said main portion. The seat for the battery housed in main portion 59 of the casing is accessible from the outside through a cover 60.

Main portion 59 has a substantially constant cross-section along an axis parallel to primary rod 17 and interface portion 61 has a bell-shaped cross-section that widens in a direction away from main portion 59 and parallel to the axis of primary rod 17.

Bell-shaped interface portion 61 is open at its opposed ends and has a side wall 62 without openings. The wider opening of interface portion 61 is closed by the second plate 21 provided with engagement seats 23a, 23b for syringes 27a, 27b. A sealing gasket 63 preventing the inlet of liquids and humidity into interface portion 61 is provided between the peripheral edge of plate 21 and the rim of the opening of interface portion 61. In the illustrated embodiment, the first plate 13 is located between interface portion 61 and main portion 59 of casing 57. A first sealing gasket 65 preventing the inlet of humidity and liquids coming from the outside into interface portion 61 is provided between the peripheral edge of the first plate 13 and the adjacent surface of the edge of main portion 59. Similarly, a second sealing gasket 67 preventing the inlet of humidity and liquids coming from the outside into main portion 59 is provided between the peripheral edge of the first plate 13 and the adjacent surface of the edge of main portion 59. In this manner, advantageously, main portion 59 of casing 57 is substantially tightly sealed with respect to the environment outside device 11.

The device as described and shown can undergo several variations and modifications lying within the same inventive principle.

The invention claimed is:

1. A syringe actuating device (11), comprising:
   a first supporting plate or frame (13) in which a first axial guide (15) for a primary rod (17) is defined;
   a second supporting plate or frame (21) defining at least two engagement seats (23a, 23b) for bases (25) of corresponding syringes (27a, 27b) having a syringe barrel (55) and a sliding plunger (53), a second axial guide (26) for axial sliding of a corresponding secondary rod (29a, 29b) having a head (51) being associated with each of the engagement seats (23a, 23b);
   an electric motor (37) having a driving shaft (39);
   an assembly for converting rotary motion of the driving shaft (39) of the electric motor (37) into an axial sliding of the primary rod (17); and
   at least one pair of connecting arms (49a, 49b) adapted to transmit the axial sliding of the primary rod (17) to a corresponding one of said secondary rods (29a, 29b), whereby the rotary motion of the driving shaft (39) of the electric motor (37) causes the axial sliding of the secondary rods (29a, 29b) and, consequently, sliding of the plungers (53) of the syringes (27a, 27b), when said syringes are engaged in the corresponding engagement seats (23a, 23b) and the plungers (53) are in abutment against said heads (51);

wherein each of the secondary rods (29a, 29b) has a smooth external surface and the second supporting plate (21) is provided, at each engagement seat (23a, 23b) for the syringe, with a ferrule (28) defining said second axial guide (26) for the axial sliding, the ferrules (28) being monolithically formed with the second supporting plate (21), and a sealing gasket (19) determining a tight seal between the ferrules (28) and the corresponding secondary rod (29a, 29b) and preventing humidity and liquids from passing through the ferrules (28) being provided between the ferrules (28) and the corresponding secondary rods (29a, 29b);

wherein the engagement seats (23a, 23b) are adapted to receive the bases (25) of the corresponding syringes (27a, 27b) which are provided with radially projecting wings (31) and define female parts of bayonet-like couplings for the corresponding syringes (27a, 27b);

wherein the first and the second supporting plate (13, 21) are parallel to each other and are firmly associated with each other along a perimeter of each of the first and second supporting plates (13, 21) inside a casing (57) of the device (11);

wherein the casing (57) comprises a main portion (59), in which the motor (37) and the assembly for converting rotary motion are housed, and an interface portion (61), which is connected to the main portion (59) and to which the second supporting plate (21) is tight-sealingly associated;

wherein the main portion (59) has a constant cross-section along an axis parallel to the primary rod (17) and the interface portion (61) has a bell-shaped cross-section that widens in a direction away from the main portion (59) and parallel to the axis of the primary rod (17);

wherein the first supporting plate (13) is tight-sealingly attached, along the perimeter of the first supporting plate (13), to an internal wall of the casing (57), whereby the main portion (59) of the casing (57) is tight-sealingly insulated from an environment outside the device (11);

wherein a sealing gasket (63) is positioned between a peripheral edge of the second supporting plate (21) and a rim of the interface portion (61), a sealing gasket (65) is positioned between a peripheral edge of the first supporting plate (13) and an edge of the interface portion (61), and a sealing gasket (67) is positioned between the peripheral edge of the first supporting plate (13) and an edge of the main portion (59); and wherein the second supporting plate (21) is solid without any through-hole openings except as provided by the ferrules (28).

2. The device according to claim 1, wherein the sealing gasket (19) provided between the ferrules (28) and the secondary rods (29a, 29b) includes an O-ring.

3. The device according to claim 2, wherein the assembly for converting rotary motion comprises a pinion (41) associated with the driving shaft (39) of the electric motor (37) and a gear ring (43) engaged in the pinion (41) and surrounding an internally threaded screw nut (45) cooperating with an outer thread of the primary rod (17), wherein the rotation of the screw nut (45), caused by the rotation of the gear ring (43) induced by the pinion (41) and the driving shaft (39) of the electric motor (37), causes the axial sliding of the primary rod (17) passing through the first supporting plate (13) at the first axial guide (15) and, through the connecting arms (49a, 49b), the axial sliding of the secondary rods (29a, 29b) passing through the second supporting plate at the second axial guide (26).

4. The device according to claim 3, wherein the screw nut (45) is rotatably supported by a third supporting plate or frame (47) of the device (11), a thrust ball bearing (48) being provided between said third plate (47) and the screw nut (45).

5. The device according to claim 4, wherein the connecting arms (49a, 49b) are arranged perpendicular to the primary rod (17) and the secondary rods (29a, 29b) and wherein a unit consisting of the primary rod (17), the connecting arms (49a, 49b) and the secondary rods (29a, 29b) defines a fork-like configuration.

6. The device according to claim 1, wherein the assembly for converting rotary motion comprises a pinion (41) associated with the driving shaft (39) of the electric motor (37) and a gear ring (43) engaged in the pinion (41) and surrounding an internally threaded screw nut (45) cooperating with an outer thread of the primary rod (17), wherein the rotation of the screw nut (45), caused by the rotation of the gear ring (43) induced by the rotation of the pinion (41) and the driving shaft (39) of the electric motor (37), causes the axial sliding of the primary rod (17) passing through the first supporting plate (13) at the first axial guide (15) and, through the connecting arms (49a, 49b), the axial sliding of the secondary rods (29a, 29b) passing through the second supporting plate at the second axial guide (26).

7. The device according to claim 6, wherein the screw nut (45) is rotatably supported by a third supporting plate or frame (47) of the device (11), a thrust ball bearing (48) being provided between said third plate (47) and the screw nut (45).

8. The device according to claim 1, wherein the connecting arms (49a, 49b) are arranged perpendicular to the primary rod (17) and the secondary rods (29a, 29b) and wherein a unit consisting of the primary rod (17), the connecting arms (49a, 49b) and the secondary rods (29a, 29b) defines a fork-like configuration.

9. A syringe actuating device (11), comprising:
a first supporting plate or frame (13) in which a first axial guide (15) for a primary rod (17) is defined;
a second supporting plate or frame (21) defining at least two engagement seats (23a, 23b) for bases (25) of corresponding syringes (27a, 27b) having a syringe barrel (55) and a sliding plunger (53), a second axial guide (26) for axial sliding of a corresponding secondary rod (29a, 29b) having a head (51) being associated with each of the engagement seats (23a, 23b);
an electric motor (37) having a driving shaft (39);
an assembly for converting rotary motion of the driving shaft (39) of the electric motor (37) into an axial sliding of the primary rod (17); and
at least one pair of connecting arms (49a, 49b) adapted to transmit the axial sliding of the primary rod (17) to a corresponding one of said secondary rods (29a, 29b), whereby the rotary motion of the driving shaft (39) of the electric motor (37) causes the axial sliding of the secondary rods (29a, 29b) and, consequently, sliding of the plungers (53) of the syringes (27a, 27b), when said syringes are engaged in the corresponding engagement seats (23a, 23b) and the plungers (53) are in abutment against said heads (51);
wherein each of the secondary rods (29a, 29b) has a smooth external surface and the second supporting plate (21) is provided, at each engagement seat (23a, 23b) for the syringe, with a ferrule (28) defining said second axial guide (26) for the axial sliding, the ferrules (28) being monolithically formed with the second supporting plate (21), and a sealing gasket (19) providing a tight seal between the ferrules (28) and the corresponding secondary rod (29*a*, 29*b*) and preventing humidity and liquids from passing through the ferrules (28) being provided between the ferrules (28) and the corresponding secondary rods (29*a*, 29*b*);

wherein the first and the second supporting plate (13, 21) are parallel to each other and are firmly associated with each other along a perimeter of each of the first and second supporting plates (13, 21) inside a casing (57) of the device (11);

wherein the casing (57) comprises a main portion (59), in which the motor (37) and the assembly for converting rotary motion are housed, and an interface portion (61), which is connected to the main portion (59) and to which the second supporting plate (21) is tight-sealingly associated;

wherein the main portion (59) has a constant cross-section along an axis parallel to the primary rod (17) and the interface portion (61) has a bell-shaped cross-section that widens in a direction away from the main portion (59) and parallel to the axis of the primary rod (17);

wherein the first supporting plate (13) is tight-sealingly attached, along the perimeter of the first supporting plate (13), to an internal wall of the casing (57), whereby the main portion (59) of the casing (57) is tight-sealingly insulated from an environment outside the device (11);

wherein a sealing gasket (63) is positioned between a peripheral edge of the second supporting plate (21) and a rim of the interface portion (61);

wherein a sealing gasket (65) is positioned between a peripheral edge of the first supporting plate (13) and an edge of the interface portion (61); and wherein a sealing gasket (67) is positioned between the peripheral edge of the first supporting plate (13) and an edge of the main portion (59); and wherein the second supporting plate (21) is solid without any through-hole openings except as provided by the ferrules (28).

* * * * *